US008552401B2

(12) United States Patent
Kane

(10) Patent No.: US 8,552,401 B2
(45) Date of Patent: Oct. 8, 2013

(54) OPTICAL CHEMICAL SENSOR FEEDBACK CONTROL SYSTEM

(75) Inventor: James A Kane, Needham Heights, MA (US)

(73) Assignee: Polestar Technologies, Inc., Needham Heights, MA (US)

( * ) Notice: Subject to any disclaimer, the term of this patent is extended or adjusted under 35 U.S.C. 154(b) by 596 days.

(21) Appl. No.: 12/348,421

(22) Filed: Jan. 5, 2009

(65) Prior Publication Data

US 2010/0032583 A1    Feb. 11, 2010

Related U.S. Application Data

(63) Continuation-in-part of application No. 11/113,464, filed on Apr. 25, 2005, now abandoned.

(51) Int. Cl.
*G01N 21/64* (2006.01)

(52) U.S. Cl.
USPC ...................................................... 250/458.1

(58) Field of Classification Search
USPC ............ 250/458.1, 201.1, 581, 585, 586, 587
See application file for complete search history.

(56) References Cited

U.S. PATENT DOCUMENTS

| | | | | |
|---|---|---|---|---|
| 5,863,460 A * | 1/1999 | Slovacek et al. | ......... | 252/301.35 |
| 5,957,858 A * | 9/1999 | Micheels et al. | .............. | 600/529 |
| 6,043,506 A * | 3/2000 | Heffelfinger et al. | ......... | 250/584 |
| 6,285,807 B1 * | 9/2001 | Walt et al. | ........................ | 385/12 |
| 6,426,505 B1 * | 7/2002 | Rao et al. | .................... | 250/458.1 |
| 6,787,110 B2 * | 9/2004 | Tiefenthaler | ..................... | 422/91 |
| 7,041,493 B2 * | 5/2006 | Rao | .............................. | 435/288.1 |
| 2002/0025547 A1 * | 2/2002 | Rao | .............................. | 435/40.5 |
| 2002/0160522 A1 * | 10/2002 | Rubinstein et al. | ........... | 436/164 |

* cited by examiner

*Primary Examiner* — David Porta
*Assistant Examiner* — Casey Bryant
(74) *Attorney, Agent, or Firm* — Burns & Levinson LLP; Orlando Lopez

(57) ABSTRACT

An optical chemical sensor feedback control system is provided comprised of a luminescent sensing film, an optical processor adjacent the sensing film capable of sinusoidally photoexciting the luminescent sensing film and detecting the luminescent emission resulting therefrom, and a computer control means executing a computer program, in communication with the optical processor. The computer control means is operable to control the magnitude of the photoexcitation of the luminescent sensing film, wherein the computer control means receives data regarding the luminescent emission resulting therefrom, analyzes same, and determines the magnitude and phase shift of the luminescence relative to the photoexcitation. Further, the system herein is operable to determine the status of the sensing film, and adjust the magnitude of photoexcitation thereof based on same. In addition, the system, via the optical processor positioning means, is operable to adjust the physical position of the optical processor and/or light source in relation to the sensing film, based on data received from the computer control means.

16 Claims, 5 Drawing Sheets

OPTICAL CHEMICAL SENSOR FEEDBACK CONTROL SYSTEM

CROSS-REFERENCE TO A RELATED APPLICATION

This application is a continuation-in-part application of copending application Ser. No. 11/113,464, filed Apr. 25, 2005, the contents of which are incorporated herein by reference.

FIELD OF THE INVENTION

An optical chemical sensor feedback control system for controlling optical sensing systems utilizing phase-sensitive fluorescence lifetime measurement in the detection process is provided. In particular, an optical chemical sensor feedback control system is provided which measures the luminescent emission of sensing films with respect to the level of photoexcitation thereof, monitors the status of the sensing film over time, adjusts the magnitude of the sensing film based on same (to, for example, compensate for photobleaching), and adjusts and/or replaces sensors (i.e., sensing films) in the system as needed.

BACKGROUND OF THE INVENTION

Optical chemical sensors have been developed for monitoring the concentration of a variety of chemical constituents, including molecular $O_2$, pH and carbon dioxide. These sensors have significant advantages over the more traditional electrochemical sensors, such as electrical isolation from the environment measured, small size, immunity to calibration drift arising from sensing membrane fouling, and compatibility with non-contacting measurements. Applications include, for example, monitoring conditions within fermentation and cell culture bioreactors, and ultra-pure water, such as is used in the fabrication of semiconductors.

Although such conventional optical chemical sensors are extremely effective in monitoring various concentrations in a variety of situations, various deficiencies are encountered with the use thereof. For example, conventional optical chemical sensors experience photobleaching over time, thereby requiring the frequent replacement or service of the sensors. However, in conventional systems, the replacement or service of optical chemical sensors is a laborious, time consuming effort.

Furthermore, when repairing or replacing conventional optical chemical sensors, a portion of, or even the entire system/process, must be shut down to enable replacement or service of the sensors. Moreover, depending on the nature of the system under investigation, replacement or service of the sensor may be impossible, and failure of the sensor may lead to a complete overhaul of the system, such as emptying the system of all components, cleaning the entire system thoroughly, and restarting the system from scratch.

In view of the disadvantages associated with the use of conventional optical chemical sensors in environments such as fermentation and cell culture bioreactors, it is an object of the present invention to provide an optical chemical sensor feedback control system which can determine the proportional luminescent emission response of sensors (such as sensing films).

It is a further object of the invention to provide an optical chemical sensor feedback control system which is capable of monitoring the status (i.e., the luminescent emission response) of the luminescent sensing film, and adjust the magnitude of the photoexcitation thereof accordingly, so as to obtain satisfactory luminescent emission data.

It is a further object of the present invention to provide an optical chemical sensor feedback control system which, when the system determines that the luminescent sensing film is exhibiting an unsatisfactory response, can adjust and/or replace the optical chemical sensors as needed, while eliminating and/or minimizing disturbance to the environment monitored.

It is another object of the present invention to provide a method of feedback control of an optical chemical sensor, wherein the optical sensor, comprising a luminescent sensing film, is utilized, monitored, and replaced/adjusted as needed, and the magnitude of the photoexcitation thereof is adjusted based on calibration data and historical luminescent emission response data.

SUMMARY OF THE INVENTION

In order to achieve the objects of the present invention as described above, the present inventor earnestly endeavored to provide an optical chemical sensor feedback control system, and method of feedback control of an optical chemical sensor. In doing so, the present inventor developed an optical chemical sensor feedback control system operable to determine the magnitude of the luminescent response of, as well as control/monitor the status of, a sensing element or portion of the material or sensing membrane. It was unexpectedly discovered that, when using the device of the present invention, any type of chemical sensing materials can be controlled/monitored, such as $O_2$ sensors, pH sensors, glucose sensors, temperature sensors, carbon dioxide, pressure, etc.

Accordingly, in a first embodiment of the present invention, an optical chemical sensor feedback control system is provided, comprising:

(a) a luminescent sensing film;

(b) an optical processor adjacent said sensing film comprising:
  (i) a light source for luminescent photoexcitation of said sensing film, and
  (ii) a photodetector for detection of luminescent emission of said sensing film;

(c) a computer control means in communication with the optical processor, said computer control means operable to transmit commands concerning positioning of the light source and luminescent sensing films, and frequency and magnitude of the luminescent photoexcitation by the light source;

(d) a computer program product operable to be executed on the computer control means, said computer program product comprising a computer useable medium embodying computer useable program code for initiating a sampling cycle, controlling the magnitude of the luminescent photoexcitation (fluorescence signal magnitude) of the luminescent sensing film by the light source, monitoring the status (condition) of the sensing film, receiving parameter sensitive luminescent emission signal data, and determining magnitude and phase shift of resulting luminescent emissions relative to the luminescent photoexcitation; and (e) an optical processor positioning means in communication with the computer control means and the optical processor, said optical processor control means operable to adjust the physical position of the optical processor in relation to the luminescent sensing film based on the commands received from the computer control means.

In a further embodiment of the present invention, the computer program product is operable to determine the status (condition) of the luminescent film. For example, over time, most luminescent sensing films tends to degrade due to photobleaching. This degradation of the film leads to decreased responsiveness (luminescent emission) on the part of the film in response to photoexcitation thereof. In order to determine the status of the luminescent sensing film, the computer program performs the following functions:

(i) Determines the status of the luminescent sensing film by analyzing historical luminescent emission signal data, so as to determine a level of decrease in luminescent emissions of the luminescent sensing film over time. The historical luminescent emission signal data is stored on a computer readable database, which is in communication with the computer control means. This analysis process may further take into account the calibration process data, so as to determine a base level of luminescent emission response; and (j) The computer program then generates a user report, wherein the user report comprises data concerning the status of the luminescent sensing film. For example, the user report may provide a chart illustrating luminescent emission of the film over time, so as to illustrate to the user the rate of degradation of the film in response to photoexcitation thereof.

In yet a further embodiment of the present invention, the computer program product, in response to user commands, is operable to calculate appropriate drive signals (to be transmitted to the light source), based on calibration data of the sensing film, and/or historical luminescent emission data. For example, if a user enters a command requesting photoexcitation of the luminescent sensing film at a particular wavelength, the computer program of the present invention is operable to calculate, based on historical luminescent emission data of the particular film in question, the appropriate magnitude of photoexcitation to be applied to the film by the light source.

This functionality of the computer program is achieved by performing the following function:

(k) A third drive signal command is generated, by first determining the status (condition) of the luminescent sensing film. This calculation is performed by accessing a database of historical luminescent emission data, and determining the status of the film at the end of the most recent sampling cycle. The status of the film is then compared to the desired level of photoexcitation, so as to determine the desired magnitude and phase shift of luminescent emissions by the sensing film relative to the magnitude and phase shift of the photoexcitation thereof in prior sampling cycle.

The luminescent film is comprised of a polymeric material having a luminescent indicating composition disposed on, incorporated within, or adhered to the polymeric material (collectively referred to as a polymeric substrate). The polymeric substrate is preferably a silicone, polyurethane, polycarbonate, nylon, polystyrene, polyester, polyolefin, polyacrylamide, cellulose, epoxy, vinyl, natural rubber or a sol gel.

As mentioned above, the luminescent indicating composition may be any sensing composition capable of utilization in the detection of $O_2$, pH, glucose, temperature, carbon dioxide, pressure, etc. Preferably, the luminescent indicating composition is comprised of one or more of fluorescein and fluorescein derivatives such as carboxyfluorescein, rhodamine, seminaphtharhodamine, seminaphthafluorescein, hydroxyprene trisulfonic acid, organometallic complexes and tethered-pair indicators.

With regards to the organometallic complexes, preferably, one or more of organometallic transition metal complexes is utilized, including complexes of platinum, palladium, ruthenium, osmium, iridium, rhodium rhenium and chromium, and lanthanide series complexes including complexes of terbium, europium, and erbium.

The light source may be any light source capable of luminescently photoexciting the luminescent sensing film. Preferably, the light source is an LED, organic LED, incandescent bulb, laser, flashlamp, and/or an electroluminescent device. The light source, however, need not be in direct luminescent communication with the luminescent sensing film.

Rather, the light source may be in communication with a fiber optic, wherein the fiber optic redirects the light at/towards the luminescent sensing film, thereby allowing the light source to be disposed remotely with respect to the luminescent sensing film. This, disposition is preferable in applications in which the ease of repair and/or replacement of the light source dictates the disposition of the light source in a location apart from the luminescent sensing film.

The photodetector of the present invention may be any conventional photodetecting means capable of detecting light energy in the spectrum of analysis of interest. However, preferably, the photodetector is a silicon photodiode, an avalanche photodiode, or photomultiplier tube.

The optical processor positioning means functions to adjust the physical position of the optical processor in relation to the luminescent sensing film, based on commands received from the computer control means. For example, if the system determines that the luminescent sensing film is no longer sufficiently responsive to photoexcitation, the optical processor positions means may be commanded to remove the currently used luminescent sensing film, and replace same with a new (fresh) luminescent sensing film.

To provide such functionality, the optical processor positioning means is comprised of a control means communication link in communication with the computer control means, and an optical processor position adjustment device in communication with the control means communication link. The optical processor position adjustment device may be any conventional adjustment device capable of adjusting the position of the luminescent sensing film. Preferably, the optical processor positioning device is comprised of one or more of a stepper motor, a pneumatic piston, a hydraulically driven piston, an electric motor and a mechanical motor.

DETAILED DESCRIPTION OF THE INVENTION

Figure 1:
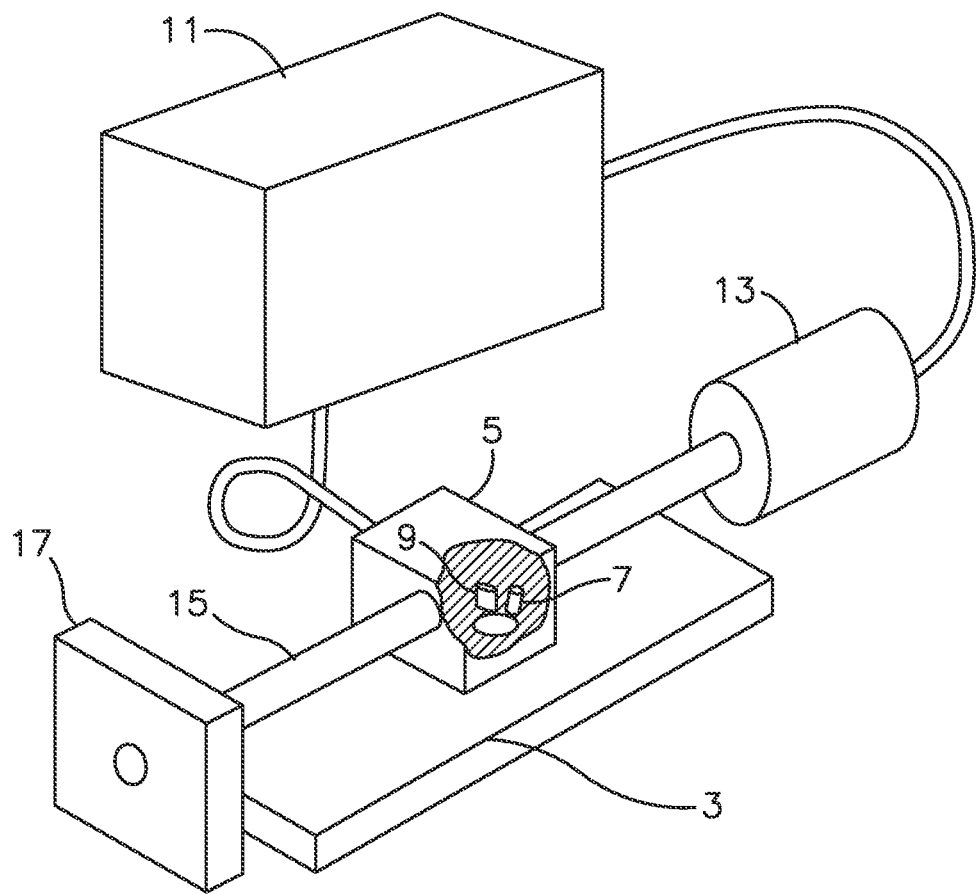
FIG. 1 is a perspective view of the optical processor positioning means of the present invention, illustrating the use of a linear positioner design as the optical processor positioning means. In particular, in this example, a lead screw is used to translate rotary motion into linear motion by mounting the optical processor to the lead screw via a bearing such that the optical processor can be moved along the length of the sensing film by rotating the lead screw with the stepper motor.

As mentioned above, many conventional feedback control systems utilize fluorescence lifetime-based optical sensors to monitor the concentration of a variety of chemical constituents, such as molecular $O_2$, pH and carbon dioxide. These optical sensors contain sensing membrane(s) which need replacement and/or servicing on a regular basis. In order to overcome this problem, the optical chemical sensor feedback control system 1 of the present invention allows a user thereof to monitor the status (condition) of the sensing film, and adjust the magnitude of photoexcitation thereof to compensate for degradation in the responsiveness of the film over time.

In addition, the system is operable to enable a user to conveniently exchange the sensing membrane with a fresh sensing film 3 or, alternatively, move the optical interrogation system (referred to herein as the optical processor 5) adjacent to a section of the sensing membrane that has not been adversely affected by overuse or environmental causes, such as excessive photobleaching.

For example, under repeated light exposure, the fluorescence indicator molecules of the luminescent sensing film undergoes degradation as a result of photobleaching. This process destroys indicator molecules, thereby rendering them non fluorescent as illustrated by a reduction in fluorescence signal magnitude for a given excitation light level. The present system is operable to measure this level of non-fluorescent, so as to assess the status (condition) of the sensing film, and the level of depletion thereof.

In particular, as illustrated in FIGS. 1-4, the optical chemical sensor feedback control system 1 of the present invention uses measurements of signal intensity, in conjunction with phase-shift detection, as a means of monitoring the parameter of interest and the status (condition) of the sensing membrane (sensing film 1). This is achieved, mechanically, by interfacing the optical processor 5 with a computer-controlled positioning system 19, so as to enable automatic relocation of the optical processor 5 (having a light source to photoexcite the sensing membrane 3 and a photodetector 9 to measure the luminescent emission produced thereby) to a fresh (active) area of the sensing membrane in response to low signal levels (i.e., low luminescent emission levels).

To achieve the system functionality described above, as shown in FIG. 1, the optical chemical sensor feedback control system 1 comprises a luminescent sensing film 3, and an optical processor 5 positioned adjacent the luminescent sensing film 3, the optical processor 5 having a light source 7 capable of photoexciting the sensing film 3, and a photodetector 9 for detecting the luminescent emission of the sensing film 3. The system 1 further comprises a computer control means 11 in communication with the optical processor 5, which controls the magnitude of the photoexcitation of the sensing film 3, the status (condition) of the film 3, receives parameter sensitive luminescent emission signals via the photodetector 9, and generates data and/or commands (in the form of electrical signals) based on same to determine the magnitude and phase shift of the luminescence of the sensing film 3 relative to the photoexcitation of the sensing film 3 by the optical processor 5.

The system 1 further comprises an optical processor positioning means 13 in communication with the computer control means 11 and the optical processor 5. The computer control means 11, when determining that the sensing membrane 3 is no longer performing satisfactorily via feedback provided by either direct measurements of fluorescence signal magnitude during sinusoidal excitation of the sensing chemistry or by electronically controlled corrections to the amplitude of the fluorescence excitation source to maintain fixed amplitudes of recovered fluorescence signals, causes (via commands transmitted thereto) the optical processor positioning means 13 to adjust the position of the optical processor 5 relative to the luminescent sensing film 3.

Figure 2:
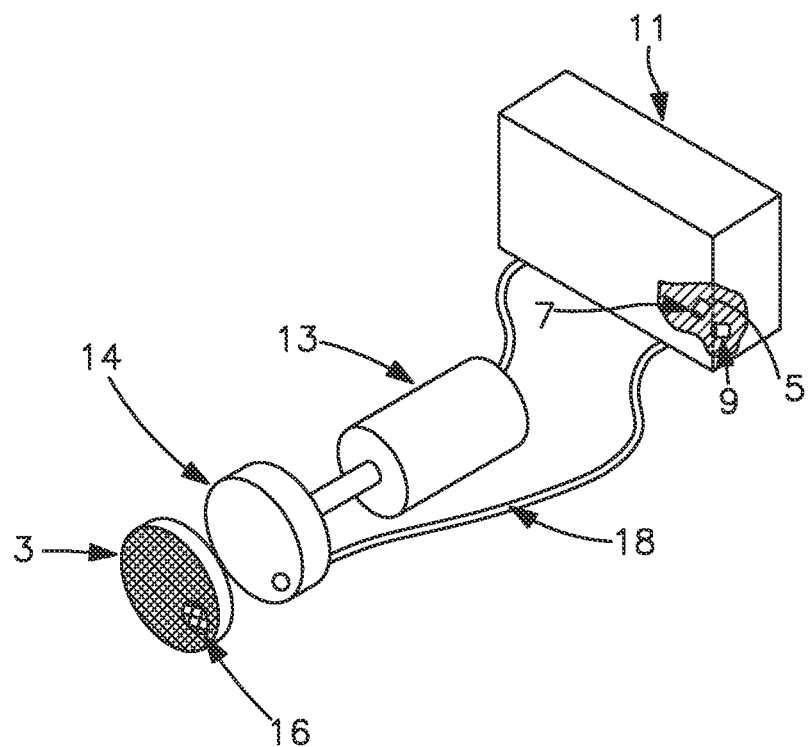
FIG. 2 is a perspective view of the optical processor positioning means of the present invention, illustrating the use of a rotational positioning motion means to reposition the optical processor's fiber optic element with respect to the sensing film being utilized, such that the area of illumination of the sensing film can be changed over time. As described above, the fiber optic is an example of a conduit over which optical excitation and fluorescent emission signals can be communicated.

Alternatively, as illustrated in FIG. 2, an optical conduit, such as a fiber optic 17, may be used to limit the area of sensing film 3 under examination, by repositioning the fiber optic 17 by means of a fiber optic positioner 13 in conjunction with optical processor positioning means 19. This method may also be employed when using a linear positioning means, such as that used in the system 1 shown in FIG. 1, as moving a fiber optic attached to the lead screw in FIG. 1 would reposition the light source 7 relative to the sensing film 3.

In particular, as illustrated in FIG. 2, the optical processor positioning means 13 may be in the form of a rotational positioning device such as a stepper motor that can be manipulated/commanded by the control means 11 to move a fiber optic light source 7 via a fiber optic positioner 13 relative to a fixed luminescent sensing film 3 when the computer control means 11 determines that the effective lifetime of the area of illumination 15 of the luminescent sensing film 3 has expired. Thus, when the area of illumination 15 of the luminescent film 3 is no longer performing optimally, a new, unused, active portion of the luminescent sensing film 3 is exposed to the light source 7 of the optical processor 5.

Figure 3:
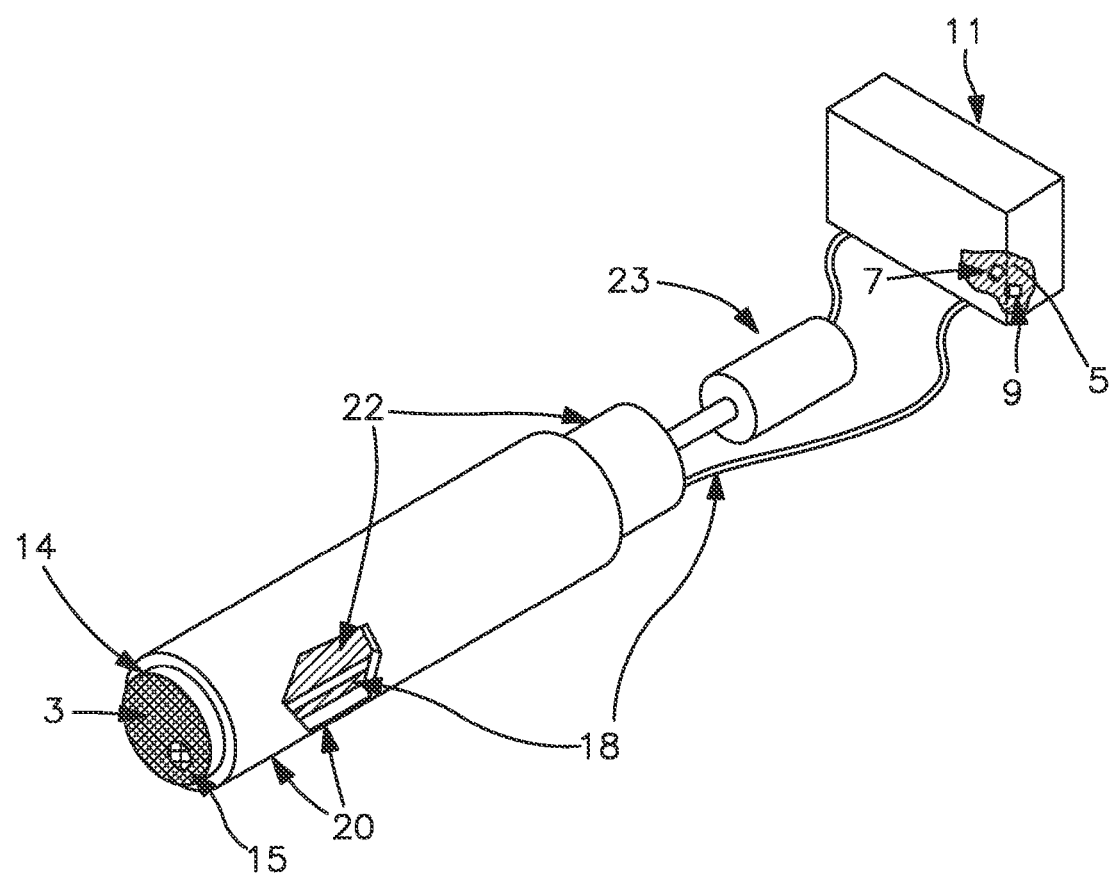
FIG. 3 is perspective view of the optical processor positioning means of the present invention, illustrating the use of a rotational positioning motion in conjunction with a cylindrical probe that houses a luminescent sensing film. The probe includes a cylindrical inner body element positioned within a cylindrical outer body to which is attached the fluorescent sensing film. A fiber optic element is attached to the inner body in such a way as to allow a new area of the sensing film to be illuminated by rotating the inner body within the outer body element.
Figure 4:
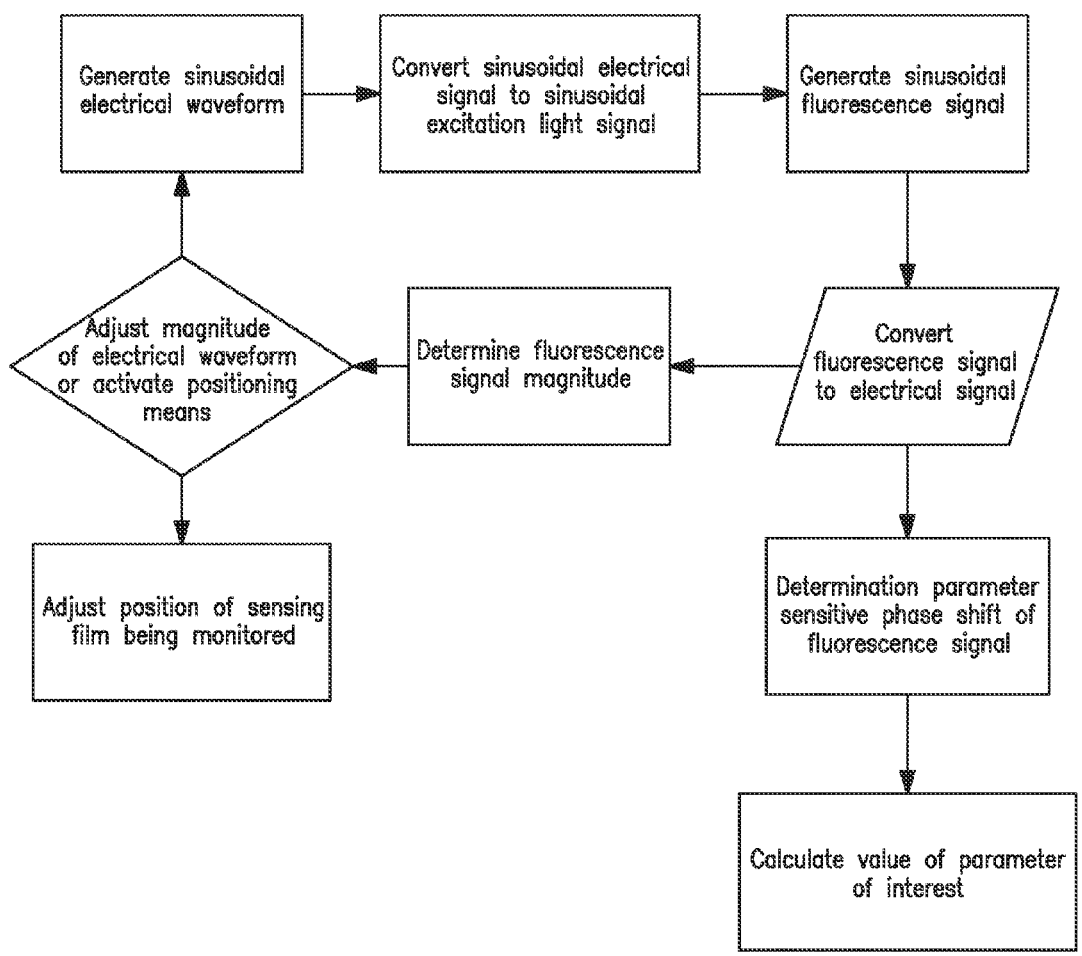
FIG. 4 is a flow diagram illustrating the general functional steps of the computer program product of the present invention.

In a further embodiment, as disclosed in FIG. 3, herein, a probe design is provided, wherein a luminescent sensing film 13 is attached to the end of a probe outer body 17, designed to allow the insertion of a probe inner member 19 which holds the end of a fiber optic cable 21 at the distal end of the probe outer body 17, thus enabling the communication of optical signals between an optical processor 5 and the sensing film 13. The portion of the sensing film being observed 15 is determined by the position of the fiber optic 21, which can be changed by rotating the probe inner body 19 with respect to the outer body 20 using the optical processor positioning means 23.

As the light source for photoexciting the luminescent sensing film 3, an LED, organic LED, incandescent bulb, flashlamp, or electroluminescent display may be used. The luminescent emission caused by the photoexcitation of the luminescent sensing film 3 is converted to an electrical signal via a silicon photodiode, an avalanche photodiode or a photomultiplier tube. The method of the present invention further involves determining the magnitude of the electrical signal via the computer control means 11, by using either analog or digital methods (and means as described above).

Furthermore, the light source may by disposed so as to photoexcite the luminescent sensing film via a fiber optic, as illustrated in FIGS. 2 and 3 herein. The use of a fiber optic allows the area of photoexcitation to be limited and specifically defined, and allows the light source to be located remotely from the sensing film.

As mentioned above, the monitoring and determination of the status of the luminescent sensing film is carried out by the computer control means via execution of the computer program product of the present invention. In general, the computer control means is a computer system which may include, inter alia, one or more computers and at least a computer readable medium, allowing the computer system, to read data, instructions, messages or message packets, and other computer readable information from the computer readable medium. The computer readable medium may include non-volatile memory, such as ROM, flash memory, disk drive memory, CD-ROM, and other permanent storage. Additionally, a computer readable medium may include, for example, volatile storage such as RAM, buffers, cache memory, and network circuits. Furthermore, the computer readable medium may comprise computer readable information in a transitory state medium such as a network link and/or a network interface, including a wired network or a wireless network that allows a computer system to read such computer readable information.

The computer of the computer control means may be any conventional computing means capable of carrying out the functions of the computer program product described above. For example, any conventional digital microprocessors, such as an Intel® 386 microprocessor or above (in computing power), may be utilized. Further, the computer control means may be provided in the form of a conventional IBM-compatible laptop or other type of personal computer (e.g., notebook, desk top, mini-tower, Apple Macintosh, palm pilot, etc.), preferably equipped with a user interface means, such as a keyboard and a mouse.

The computer system may utilize any of the major platforms (e.g., Linux, Macintosh, Unix, OS2, etc.), but preferably includes a Windows environment (e.g., Windows XP or Vista). Further, the computer control means may include other conventional components (e.g. processor, disk storage or hard drive, etc.) having sufficient processing and storage capabilities to effectively execute the system software (computer program product), and having the computing power necessary to carry out such calculations. However, alternatively, a conventional analog feedback loop may be utilized for simple applications, so as to minimize cost.

The computer control means may further comprise a display interface that forwards graphics, text, and other data from the communication infrastructure for display on a display unit (i.e., a graphical user interface). The computer control means also preferably includes a main memory, preferably random access memory (RAM), and may also include a secondary memory. The secondary memory may include, for example, a hard disk drive and/or a removable storage drive, representing a floppy disk drive, a magnetic tape drive, an optical disk drive, etc. The removable storage drive reads from and/or writes to a removable storage unit in a manner well known to those having ordinary skill in the art. The removable storage unit, represents, for example, a floppy disk, magnetic tape, optical disk, etc. which is read by and written to by removable storage drive. As will be appreciated, the removable storage unit includes a computer usable storage medium having stored therein computer software and/or data.

In alternative embodiments, the secondary memory may include other similar means for allowing computer programs or other instructions to be loaded into the computer system. Such means may include, for example, a removable storage unit and an interface. Examples of such may include a program cartridge and cartridge interface (such as that found in video game devices), a removable memory chip (such as an EPROM, or PROM) and associated socket, and other removable storage units and interfaces which allow software and data to be transferred from the removable storage unit to the computer system.

The computer system may also include a communications interface. The communications interface allows software and data to be transferred between the computer system (computer control means) and external devices. Examples of communications interface may include a modem, a network interface (such as an Ethernet card), a communications port, a PCMCIA slot and card, etc. Software and data transferred via the communications interface are in the form of signals which may be, for example, electronic, electromagnetic, optical, or other signals capable of being received by communications interface. These signals are provided to the communications interface via a communications path (i.e., channel). This channel carries signals, and may be implemented using wire or cable, fiber optics, a phone line, a cellular phone link, an RF link, and/or other communications channels.

In this document, the terms "computer program medium," "computer usable medium," and "computer readable medium" are used to generally refer to media such as main memory and secondary memory, removable storage drives, a hard disk installed in hard disk drive, and signals. These computer program products are means for providing software to the computer system (computer control means). The computer readable medium allows the computer system to read data, instructions, messages or message packets, and other computer readable information from the computer readable medium.

The computer readable medium, for example, may include non-volatile memory, such as Floppy, ROM, Flash memory, Disk drive memory, CD-ROM, and other permanent storage. It is useful, for example, for transporting information, such as data and computer instructions, between computer systems. Furthermore, the computer readable medium may comprise computer readable information in a transitory state medium such as a network link and/or a network interface, including a wired network or a wireless network that allows a computer to read such computer readable information.

Computer programs (also called computer control logic, computer program products, software programs, etc.) are stored in main memory and/or secondary memory. Computer programs may also be received via communications interface. Such computer programs, when executed, enable the computer control means (i.e., computer system) to perform the functions of the present invention as discussed herein. In particular, the computer program, when executed, enables the microprocessor of the computer control means to perform the functions of the optical chemical sensor feedback control system described herein. Accordingly, such computer programs represent controllers of the computer system.

Unlike conventional feedback control systems, the system of the present invention, via the computer program product described above is operable to calculate the fluorescence signal magnitude (of the luminescent sensing film) during excitation, and uses the results of said calculations to control the magnitude of the excitation light (emitted by the light source) used to produce the fluorescence signal. In addition, unlike the conventional feedback control systems, the system herein is further operable to diagnose the status (condition) of the luminescent sensing film. The system herein is then operable to use these measured fluorescence signals to adjust the magnitude of the excitation light source in further sampling cycles.

The first step in this process is termed the "first sampling cycle", and is a process involving a series of functional steps that ultimately lead to the acquisition of a single reading of the fluorescence signal's (i.e., luminescent emission of the luminescent sensing film) magnitude and/or phase shift relative to the fluorescence excitation signal (i.e., the magnitude and/or phase shift of the photoexcitation by the light source).

Figure 5:
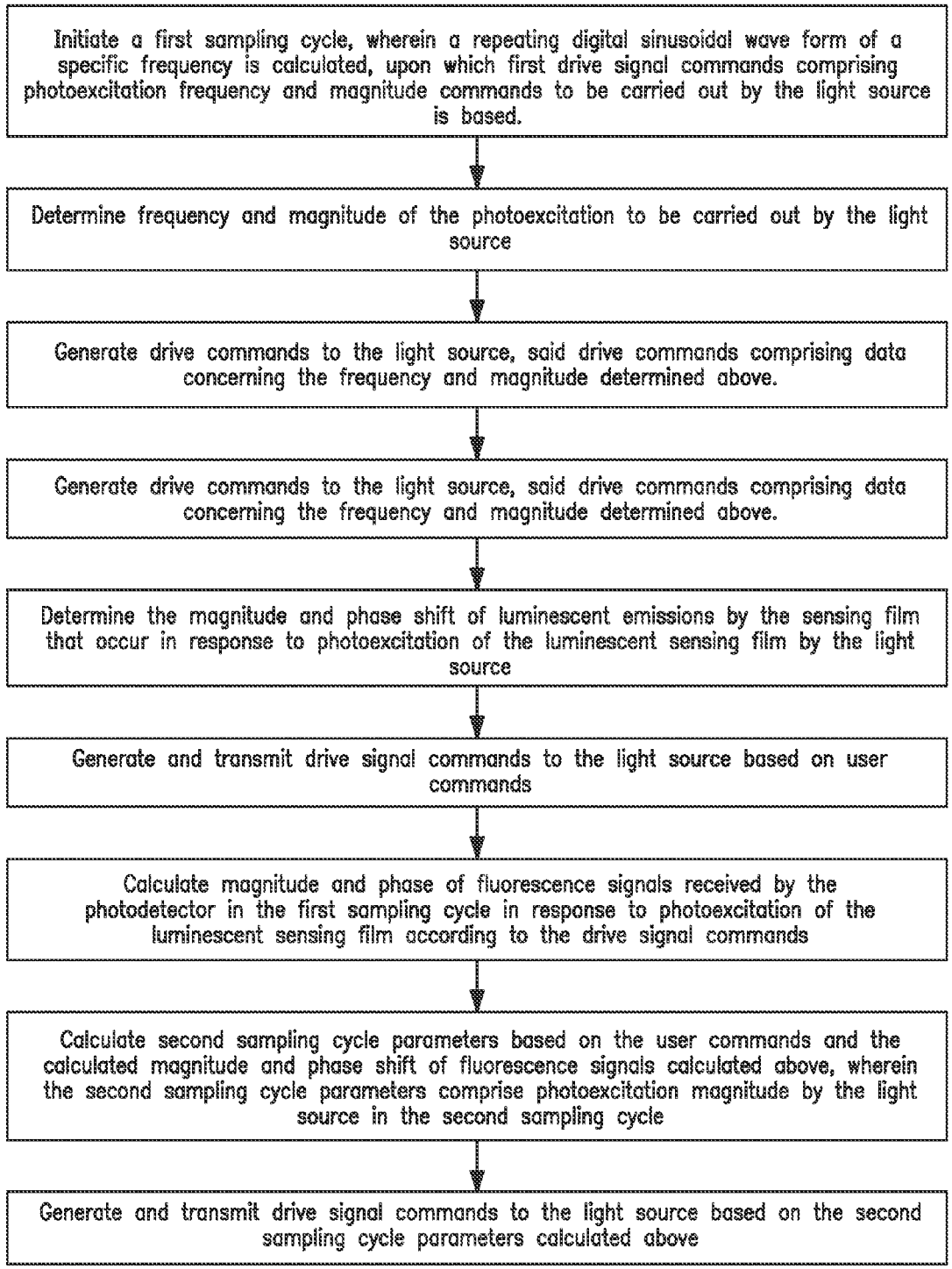
FIG. 5 is a flow diagram illustrating the general functional steps carried out by the computer program product of the present invention

In particular, as illustrated in FIG. 5, the functional steps of such process carried out by the software program of the present invention generally include (1) initiation of the sampling cycle process; (2) setting (i.e., determination) of the magnitude of the photoexcitation used to produce the fluorescence signal; (3) monitoring data collection (i.e., receiving resulting luminescent emission data from the photodetector); (4) calculating the fluorescence magnitude and phase shift values (of the luminescent emission of the luminescent sensing film), via execution of a digital lock-in algorithm; and (5) determination of the magnitude of the fluorescence excitation signal to be used in the next sampling cycle.

The "sampling" cycle performed by the present system involves a series of general functional steps which ultimately lead to the acquisition of a single reading of the fluorescence signal's magnitude and/or phase shift relative to the fluorescence excitation signal. Specifically, in the first sampling cycle, the computer program product provided by the present invention functions to carry out a calibration process, wherein the magnitude of the luminescent emission response of the luminescent sensing film is determined, relative to a series of luminescent photoexcitation events thereof, and the frequency (i.e., the frequency of photoexcitation of the luminescent sensing film) is set by the user. This calibration process, referred to herein as the first sampling cycle, is carried out by the computer useable program code to perform the following operations:

(a) Initiate a first sampling cycle, wherein a repeating digital sinusoidal wave form of a specific frequency is calculated, upon which first drive signal commands comprising photoexcitation frequency and magnitude commands to be carried out by the light source is based. The specific frequency is chosen by the user, automatically determined randomly by the computer program, or determined by the computer program based on a set of historical data (comprised of luminescent emission magnitude and phase shift vs. magnitude of photoexcitation);

(b) Determine the magnitude of the photoexcitation to be carried out by the light source;

(c) Generate drive commands, and transmit same to the light source. These drive commands comprise data concerning the frequency and magnitude determined in steps (a) and (b) above. Essentially, these drive commands control the operation of the light source, i.e., the frequency of photoexcitation thereof, and the magnitude (level) of the photoexcitation;

(d) Determine the magnitude and phase shift of luminescent emissions by the luminescent sensing film that occurs in response to photoexcitation of the luminescent sensing film by the light source. In particular, the computer control means receives the luminescent emission data from the photodetector, and the computer program product analyzes this data so as to calculate the magnitude and phase shift of luminescent emission produced by the luminescent sensing film in response to the known level (magnitude) of the photoexcitation thereof by the light source. At this point, the computer program has completed the calibration process, and the base luminescent emission response of the luminescent sensing film is now known;

(e) Thereafter, a user may choose the magnitude and frequency of further photoexcitation of the luminescent sensing film, by entering a command pertaining thereto via the computer control means. The computer program then calculates (generates) drive signal commands corresponding to these user chosen commands. These drive signal commands are then transmitted to the light source. The light source then executes these commands, thereby photoexciting the luminescent sensing film.

(f) In response to this photoexcitation, the magnitude and phase shift of fluorescence signals (i.e., luminescent emissions) produced by the luminescent sensing film, and received by the photodetector in the first sampling cycle in response to photoexcitation of the luminescent sensing film according to the drive signal commands, are calculated;

(g) Then, the magnitude and phase shift of the fluorescence signals (i.e., luminescent emissions) produced by the luminescent sensing film in the second sampling cycle (i.e., the series of photoexcitations based on the input the user commands of step (e)) is calculated. The status (condition) of the sensing film is then determined by comparing the magnitude and phase shift calculated in this step to the magnitude and phase shift of the luminescent sensing film calculated in the calibration process (i.e., in steps (a)-(d)). This results in a calculation of the level of responsiveness of the luminescent sensing film, so as to determine the change in responsiveness of same over time.

(h) Further drive signal commands (to be transmitted to the light source) are then calculated, based on the second sampling cycle parameters calculated in step (g). In particular, the computer program calculates whether the magnitude of the photoexcitation in further sampling cycles must be altered to correct for decreased (or increased) responsiveness by the luminescent sensing film. This analysis takes into consideration the calibration process data, as well as any other historical data (i.e., of prior sampling cycles) determined by the program to be relevant, or any other historical data for which a user has directed to be considered;

In a preferred embodiment, the first sampling cycle (used to determine a calibration baseline for sensing film response) is carried out on a periodic basis, with the time between samplings being set by the system (via a preset program, or via user commands). At the beginning of execution, a sampling cycle initiation signal (command) is sent by the computer control means' microprocessor to a Field Programmable Gate Array (FPGA) chip connected to a crystal oscillator which generates a voltage signal pulse train of a fixed frequency. Each oscillator pulse received by the FPGA prompts the system to output a sequential value from a look up table (stored on a database on communication with the microprocessor) of sinusoidal function values.

These sequential values are then compiled, and a repeating digital sinusoidal wave form of a specific frequency is then calculated. A drive signal (i.e., command) is then complied, comprising magnitude and frequency of the fluorescence excitation light source, based on the digital sinusoidal wave form determined previously.

It has been found that the magnitude of the resulting fluorescence signal (i.e., the luminescent emission by the luminescent sensing film) is directly proportional to the magnitude of the fluorescence excitation signal (i.e., the photoexcitation by the light source) used to produce it. The computer software program of the present invention controls the magnitude of the excitation sinusoidal by setting the value of a digital multiplier that proportionally increases the values of the digital sinusoidal waveform generated by the FPGA. The amplified sinusoidal voltage waveform is passed on to a voltage to current converter, which converts the voltage signal to a sinusoidally modulated current signal. This signal can drive the light source, for example a Light Emitting Diode (LED), so as to produce the sinusoidally modulated light signal that excites the fluorescent indicators of the sensing membrane.

The digital lock-in algorithm utilized by the computer software program provided herein to analyze the recovered fluorescence signals is based on the assumption that generating fluorescence (of the sensing film) using a sinusoidally modulated light source results in modulated fluorescence signals of exactly the same frequency as that of the excitation. This relationship enables the digital lock-in algorithm to extract the magnitude and phase shift of the fluorescence signal from a set of photodetector voltage readings of the modulated fluorescence signal taken during excitation by the modulated light source (e.g., LED). The photodetector voltage readings are proportional to the instantaneous fluorescence signal detected by the photodetector of the system (e.g., silicon photodiode, photomultiplier tube) at the time of measurement. These detector voltages are converted to a digital value using an analog-to-digital converter. These digital readings can be written to a file in memory for post processing, or alternatively fed directly into the system's microprocessor, where the lock-in algorithm is applied.

In a preferred embodiment, the system of the present invention synchronizes collection of photodetector readings to a trigger pulse from the FPGA/oscillator combination. The trigger pulse occurs at multiple, equally-spaced points during each cycle of the sinusoidal waveform. Since the trigger pulses are derived from the same function used to excite (initiate) the fluorescence, the value of the digital sinusoidal waveform that is used to generate the drive signal of the excitation light source is known at each point in the collected data set. The total number of photodetector readings collected during each sample acquisition is fixed (typically in the range of 4000 to 8000 readings). The software program is operable to count the number of readings taken, and cease the data collection process once the desired number of readings has been taken.

As mentioned above, the computer software program of the present invention is further operable to extract (i.e., calculate) the magnitude and phase shift of the luminescent emission measured in the plurality of photodetector readings described above. In particular, the magnitude (R) and phase shift (PS) of the fluorescence signal is calculated from the set of photodetector readings using the lock-in algorithm using the following expressions (formulas):

$$R = \sqrt{(X^2+Y^2)}, \quad PS = \tan^{-1}(Y/X),$$

where X and Y are the time averaged in-phase and quadrature components of the photodetector signal. The values of X and Y are calculated from the expressions;

$$X = \frac{\sum_{i=1}^{T} PR_i * \cos\theta_i}{T}, \quad Y = \frac{\sum_{i=1}^{T} PR_i * \sin\theta_i}{T},$$

where $PR_i$ are the individual digitized photodetector readings, $\cos\theta_i$ and $\sin\theta_i$ are the values of the these functions for the phase angle of the excitation signal coincident with the photodetector reading, and T is the total number of individual digitized photodetector readings acquired.

The values of $\cos\theta_i$ and $\sin\theta_i$ are stored in memory, and need not be measured since the excitation signal is derived from the same FPGA/oscillator combination used to trigger data collection.

The intensity (magnitude) of the light signal used to excite the fluorescent indicator is determined by the computer software program to provide a range of voltages generated at the photodetector that utilizes most of the range of the analog to digital converter, while never exceeding the range of voltage values that can be processed by the analog to digital converter. The preferred value for the fluorescence signal magnitude is calculated via reference to historical sampling data. Once established, the software program deems the preferred value of the fluorescence signal magnitude a "target" against which actual photodetector readings are then compared.

In the event the recovered fluorescence signal magnitude falls above or below the target value, the software program transmits a command causing the digital multiplier to be adjusted proportionally for the next sampling cycle. For example, if the target value is 100, and a digital multiplier value of 200 yields a measured fluorescence signal magnitude of 50, the software program will compile and transmit a command instructing the digital multiplier double the value to 400, so as to double the magnitude of the light signal during the next sampling cycle.

As mentioned above, photobleaching degrades the luminescent sensing film over time. Since the excitation light level required to achieve the target magnitude mentioned above is directly dependent on the number of available fluorescent indicator molecules, the excitation light level needed to reach the target value is used as a diagnostic tool for assessing the status of the sensing film depletion. Specifically, the point at which a luminescent sensing film has undergone extensive photobleaching can be readily identified by the system by determining the value of the digital multiplier used to amplify the signal used to power the light source. Intermediate levels of indicator loss can also be identified.

In order to address these issues, the system of the present invention is operable to generate and transmit user reports to the user, in which the user is provided with a notice of the status (condition) of the film, and if needed, a caution that the sensor's end of life is eminent. Accordingly, in a further embodiment of the present invention, in order to determine the status of the luminescent sensing film, the computer program performs the following functions:

(i) Determines the status of the luminescent sensing film by analyzing historical luminescent emission signal data, so as to determine a level of decrease in luminescent emissions of the luminescent sensing film over time. The historical luminescent emission signal data is stored on a computer readable database, which is in communication with the computer control means. This analysis process may further take into account the calibration process data, so as to determine a base level of luminescent emission response; and (j) The computer program then generates a user report, wherein the user report comprises data concerning the status of the luminescent sensing film. For example, the user report may provide a chart illustrating luminescent emission of the film over time, so as to illustrate to the user the rate of degradation of the film in response to photoexcitation thereof.

For example, when the system includes a digital multiplier having a range of values from 1 to 4000, with 1 generating the lowest level of excitation light and 4000 generating the maximum, the computer software program may be programmed to generate a user report when a trip point of 3500 is measured. This user report may, for example, notify the user that the sensor life is nearing its end, while a measured value of 4000 could be used to notify the user that the sensor is no longer capable of making accurate measurements. Alternatively, the computer software program may be programmed to automatically initiate relocation of the excitation light source relative the luminescent sensing film when these trip points reached predetermined values (by, or example, adjusting the light source so as to photoexcite a new section of sensing film which has not undergone appreciable photobleaching), thereby enabling the system to continue to provide accurate readings.

In addition to the system described above, a method of feedback control of an optical chemical sensor is provided by the present invention, comprising the steps of:

(a) sinusoidally photoexciting a luminescent sensing film positioned adjacent a testing environment, so as to said luminescent sensing film to emit a luminescent emission;

(b) detecting said luminescent emission, and converting said luminescent emission signal to an electrical signal via a photodetector, (c) determining the magnitude of the electrical signal via the computer control means;

(d) determining the phase of the electrical signal via a phase detector;

(e) controlling the magnitude of the sinusoidal photoexcitation of the luminescent sensing film, based on the magnitude of the electrical signal determined by the computer control means; and (f) converting the phase of the electrical signal to a parameter of interest value.

The method as described above, and as illustrated in FIG. 4 herein, involves sinusoidal excitation of a fluorescent sensing film, thus generating a sinusoidally modulated fluorescence of the same frequency, but phase-shifted relative to the light source by virtue of the sensing film's fluorescent indicator molecule's metastable excited state. These fluorescence phase-shifts are solely a function of the lifetime of the fluorescence and the modulation frequency used to excite the chemistry (i.e., the fluorescence indicator). This feature allows quantification of the parameter of interest based on measurements of the fluorescence lifetime of the indicator system, rather than measurements of the fluorescence intensity, which can vary over time as a result of the indicator photobleaching, optical misalignment, detector gain changes and/or variations in the refractive index or turbidity of the sample media being probed.

The use of the optical chemical sensor feedback control systems shown, as described above, and as illustrated in FIGS. 1-3, and the method, as described above and as illustrated in FIG. 4 herein, allow highly accurate control, and monitoring of the status of a sensing element or portion of the material or sensing membrane for various sensing materials. Sensing materials applicable include, but are not limited to, $O_2$ sensors, pH sensors, glucose sensors, temperature sensors, carbon dioxide sensors, and pressure sensors.

Advantageously, the present invention provides a system and method for controlling an optical chemical sensor feedback control system, determining the status (condition) of luminescent sensing films therein, controlling the magnitude of photoexcitation thereof based on such determinations, and controlling the physical disposition of the sensing films and/or light source. Although specific embodiments of the invention have been disclosed, those having ordinary skill in the art will understand that changes can be made to the specific embodiments without departing from the spirit and scope of the invention. The scope of the invention is not to be restricted, therefore, to the specific embodiments. Furthermore, it is intended that the appended claims cover any and all such applications, modifications, and embodiments within the scope of the present invention.

What is claimed is:

1. An optical sensor feedback control system comprising:
   (a) a luminescent sensing film;
   (b) an optical processor adjacent said sensing film comprising:
      (i) a light source for luminescent photoexcitation of said sensing film, and
      (ii) a photodetector for detection of luminescent emission of said sensing film;
   (c) a computer control means in communication with the optical processor, said computer control means operable to transmit commands concerning positioning of the light source and luminescent sensing films, and frequency and magnitude of the luminescent photoexcitation by the light source;
   (d) a computer program product operable to be executed on the computer control means, said computer program product comprising a computer useable medium embodying computer useable program code for initiating, monitoring and controlling the magnitude of the luminescent photoexcitation (fluorescence signal magnitude) of the luminescent sensing film by the light source, receiving parameter sensitive luminescent emission signal data, determining magnitude and phase shift of resulting luminescent emissions relative to the luminescent photoexcitation; diagnosing a condition of the luminescent sensing film from the magnitude; the condition of the luminescent sensing film comprising degradation of the luminescent sensing film due to photobleaching; and
   (e) an optical processor positioning means in communication with the computer control means and the optical processor, said optical processor control means operable to adjust the physical position of the optical processor in relation to the luminescent sensing film based on the commands received from the computer control means.

2. The optical sensor feedback control system of claim 1, wherein the computer program product comprises:
   (a) computer useable program code operable to initiate a first sampling cycle, wherein a repeating digital sinusoidal wave form of a specific frequency is calculated, upon which first drive signal commands comprising photoexcitation frequency and magnitude commands to be carried out by the light source is based;
   (b) computer useable program code for determining frequency and magnitude of the photoexcitation to be carried out by the light source;
   (c) computer useable program code for generating said first drive commands to the light source, said first drive commands comprising data concerning the frequency and magnitude determined in step (b);
   (d) computer useable program code operable to determine the magnitude and phase shift of luminescent emissions by the sensing film that occur in response to photoexcitation of the luminescent sensing film by the light source;
   (e) computer useable program code operable to generate and transmit second drive signal commands to the light source based on user commands;
   (f) computer useable program code operable to calculate magnitude and phase shift of fluorescence signals received by the photodetector in the first sampling cycle in response to photoexcitation of the luminescent sensing film according to the drive signal commands;
   (g) computer useable program code operable to calculate second sampling cycle parameters based on the user commands and the calculated magnitude and phase shift of fluorescence signals calculated in step (f), wherein the second sampling cycle parameters comprise photoexcitation magnitude by the light source in the second sampling cycle; and (h) computer useable program code operable to generate and transmit third drive signal commands to the light source based on the second sampling cycle parameters calculated in step (g).

3. The optical sensor feedback control system of claim 2, wherein the computer program product further comprises:

(i) computer useable program code operable to determine the status of the luminescent sensing film by analyzing historical luminescent emission signal data so as to determine a level of decrease in luminescent emissions of the luminescent sensing film over time; and (j) computer useable program code operable to generate a user report comprising data concerning the status of the luminescent sensing film.

4. The optical sensor feedback control system of claim 3, wherein the computer program product further comprises:

(k) computer useable program code operable to a generate a fourth drive signal command, based on the condition of the luminescent sensing film, and the magnitude and phase shift of luminescent emissions by the sensing film relative to the magnitude and phase shift of the photoexcitation thereof in a prior sampling cycle, said prior sampling cycle being one of said first sampling cycle or said second sampling cycle.

5. The optical sensor feedback control system of claim 1, wherein the luminescent film comprises a polymeric substrate, said polymeric substrate comprising a polymeric material and a luminescent indicating composition.

6. The optical sensor feedback control system of claim 5, wherein the polymeric substrate is a silicone, polyurethane, polycarbonate, nylon, polystyrene, polyester, polyolefin, polyacrylamide, cellulose, epoxy, vinyl, natural rubber or a sol gel.

7. The optical sensor feedback control system of claim 5, wherein the luminescent indicating composition is comprised of one or more of fluorescein and fluorescein derivatives.

8. The optical sensor feedback control system of claim 7, wherein the organometallic complex is comprised of one or more of organometallic transition metal complexes including complexes of platinum, palladium, ruthenium, osmium, iridium, rhodium rhenium and chromium, and lanthanide series complexes including complexes of terbium, europium, and erbium.

9. The optical sensor feedback control system of claim 7, wherein said fluorescein and fluorescein derivatives include at least one of carboxyfluorescein, rhodamine, seminaphtharhodamine, seminaphthafluorescein, hydroxyprene trisulfonic acid, organometallic complexes or tethered-pair indicators.

10. The optical sensor feedback control system of claim 1, wherein the light source is an LED, organic LED, incandescent bulb, laser, flashlamp, and/or an electroluminescent device.

11. The optical sensor feedback control system of claim 1, wherein the light source is in communication with the luminescent sensing film via a fiber optic.

12. The optical sensor feedback control system of claim 1, wherein the photodetector is a silicon photodiode an avalanche photodiode, or photomultiplier tube.

13. The optical sensor feedback control system of claim 1, wherein the computer control means is an analog feedback loop.

14. The optical sensor feedback control system of claim 1, wherein the control means is a digital microprocessor.

15. The optical sensor feedback control system of claim 1, wherein the optical processor positioning means comprises:

a control means communication link in communication with the computer control means; and an optical processor position adjustment device in communication with the control means communication link.

16. The optical sensor feedback control system of claim 15, wherein the optical processor position adjustment device is comprised of one or more of a stepper motor, a pneumatic piston, a hydraulically driven piston, an electric motor and a mechanical motor.

\* \* \* \* \*